United States Patent
Ginn et al.

[11] Patent Number: 5,913,866
[45] Date of Patent: Jun. 22, 1999

[54] DEVICES AND METHODS FOR HARVESTING VASCULAR CONDUITS

[75] Inventors: Richard S. Ginn, San Jose; Harry Leonard Green, II, Santa Clara, both of Calif.

[73] Assignee: Cardiothoracic Systems, Inc., Cupertino, Calif.

[21] Appl. No.: 09/032,747

[22] Filed: Feb. 27, 1998

Related U.S. Application Data

[63] Continuation-in-part of application No. 08/878,653, Jun. 19, 1997, abandoned.

[51] Int. Cl.⁶ .............................. A61B 17/36; A61B 17/32
[52] U.S. Cl. ............................................. 606/174; 606/170
[58] Field of Search .................... 606/174, 171, 606/170, 159

[56] References Cited

U.S. PATENT DOCUMENTS

| | | | |
|---|---|---|---|
| 2,668,537 | 2/1954 | Kapp | 606/174 |
| 3,837,345 | 9/1974 | Matar | 606/159 |
| 4,729,374 | 3/1988 | Alfranca | 606/171 |
| 5,101,426 | 3/1992 | Nixon | 606/159 |
| 5,522,825 | 6/1996 | Kropf et al. | 606/170 |
| 5,527,332 | 6/1996 | Clement | 606/171 |
| 5,571,131 | 11/1996 | Ek et al. | 606/170 |
| 5,628,760 | 5/1997 | Knoepfler | 606/170 |
| 5,649,947 | 7/1997 | Auerbach et al. | 606/174 |
| 5,755,723 | 5/1998 | Lombardo | 606/174 |
| 5,797,939 | 8/1998 | Yoon | 606/174 |
| 5,810,879 | 9/1998 | de Guilebon | 606/174 |

FOREIGN PATENT DOCUMENTS

| | | | |
|---|---|---|---|
| 8909029 | 10/1989 | WIPO | 606/159 |

*Primary Examiner*—Paul J. Hirsch
*Attorney, Agent, or Firm*—Lyon & Lyon LLP

[57] ABSTRACT

Devices and methods for minimally invasive harvesting of a vessel or vascular conduit, especially the saphenous vein for coronary artery bypass grafting, are disclosed. Generally, an instrument is provided which has one or more specially designed end effectors which are permanently or detachably mounted to a harvesting implement, and may also be interchangeable with each other. The end effectors have features or elements which facilitate separation of connective tissue from the vessel and/or engagement of side branches to be separated from the vessel. In various embodiments, the instrument also provides means for quickly and easily attaching and detaching the end effectors as well as means for engaging with an endoscope, if desired. The harvesting methods provide for use of the instruments through one or more minimally invasive incisions.

14 Claims, 11 Drawing Sheets

DEVICES AND METHODS FOR HARVESTING VASCULAR CONDUITS

This application is a continuation-in-part of U.S. Ser. No. 08/878,653, filed Jun. 19, 1997 now abandoned.

FIELD OF THE INVENTION

The present invention relates to surgical instruments and procedures for harvesting tissue vessels from the body, and in particular, for the minimally invasive harvesting of vascular conduits for use as a bypass graft for coronary artery bypass surgery (CABG).

BACKGROUND OF THE INVENTION

For various surgical procedures, and most commonly for coronary artery bypass grafting (CABG), it is common to remove or "harvest" a vascular conduit, such as an artery or vein, from its natural location in a patient's body and to use it elsewhere in the body. In CABG surgery, the vascular conduit is used to establish a bypass between an arterial blood source and the coronary artery being bypassed. Often, one or more of the saphenous veins in the legs are used as the vascular conduit, and is sometimes preferred by some surgeons in emergency situations, and where multiple bypass vessels are needed. Alternatively, an artery proximate the heart, such as the one of internal mammary arteries, can be used as the bypass conduit. Use of arteries rather than veins for a CABG procedure may be preferable as arteries tend to have better patency rates, and require only one anastomotic connection rather than two. For patient's requiring multiple bypasses, a surgeon may use the saphenous vein and in addition to various arteries to revascularize a patient's heart.

The conventional surgical procedure used to harvest the saphenous vein prior to its use, in a CABG procedure for example, may be very traumatic to the patient. The procedure involves making a continuous incision in the leg for the full length of the vein section to be removed in order to provide adequate exposure for visualizing the vein and for introducing tools to sever, cauterize, or ligate the branches of the vein. The incision must then be closed by suturing or stapling along its length. Major complications of the large wound such as skin loss or infections result in significant morbidity for approximately 1% of patients and frequently cause prolonged hospitalization. Other complications, such as impaired wound healing, saphenous nerve damage, hematomas, prolonged lymphatic drainage, fat necrosis with cellulitis, and chronic edema, can occur at rates exceeding 20% and are particularly costly and traumatic for a patient who has also undergone cardiac surgery. Moreover, many patients who do not suffer major complications still experience lower extremity discomfort lasting 4–6 months after the harvesting procedure. Also, ischemic and/or mechanical injury to the saphenous vein during the harvesting procedure may lead to increased rates of occlusion in the vessel graft in the months and years after the procedure. This harvesting procedure also leaves disfiguring scars, increases recovery time and the patient's hospital stay, and adds to the cost of the coronary artery surgery.

In an attempt to overcome these problems, less-invasive techniques for harvesting vessels have been developed. Most current, less-invasive techniques for dissecting a vessel employ a couple of small incisions, one at each end of the section of vessel to be removed. Blunt mechanical force is applied to first create a working space in the tissue surrounding the vein, followed by introducing tools to separate the vein from the surrounding tissue and to clip, cut, and/or cauterize side branches of the vessel. An endoscope is not necessarily required for such a procedure but may be used to enhance visualization of the vessel and the surrounding tissue and work space without having to unduly stretch the patient's skin and tissue to visualize the working space at a distance from the incision.

Even where these less invasive techniques reduce the overall length of the incision, the trauma to the vessel, the surrounding tissue, and the patient can be severe. In particular, the harvesting procedure itself may actually be lengthened and the trauma to the vessel potentially increased due to the number of tools that are needed for the harvesting procedure and which are repeatedly introduced through the incision.

The goal of the present invention is to further reduce the trauma to the patient by providing the capability to more rapidly and less traumatically harvest the vein by detaching the vein from surrounding tissue on all sides in a more expeditious procedure, minimizing the number of tools required for the procedure, and providing an harvesting device and procedure that can be effectively used and performed by a single user, while minimizing the length and number of incisions made.

SUMMARY OF THE INVENTION

The present invention provides specially designed instruments and minimally invasive procedures for the harvesting of vessels which minimize the trauma to the patient and overcome many of the drawbacks of conventional devices and procedures. In certain embodiments of the invention, a vessel harvesting assembly includes an elongated structure having two ends, and at least one end effector detachably mountable to one or both of the ends. Preferably, the elongated structure has a length substantially equal to the section of vessel to be harvested. In some of these embodiments, the elongated structure is a slender tube having a lumen sized to accommodate the scope body of an endoscope. The vessel harvesting assembly optionally includes a coupling mechanism and/or handle mechanism for locking together the harvesting tubular structure with endoscope whereby the position of the tubular structure can be fixed with respect to the tubular structure. The coupling mechanism is itself detachably mountable to the harvesting instrument.

Various detachably mountable end effectors may be employed which may be interchangeable with each other. Preferably, the end effectors have an enlarged nose portion for shielding the endoscope viewing means. At least one embodiment of an end effector has at least one edge for dissecting a vessel from surrounding connective tissue. Alternately, or in addition, the end effector has at least one hooked element configured to engage a side branch of the vessel and/or to maintain engagement with the exterior of the vessel being harvested such that the vessel provides guidance for the harvesting instrument as it moves along the vessel.

In another embodiment of the present invention, a device for harvesting a section of vessel from a the body of a patient is provided which includes an elongated structure having first and second ends and having a length substantially that of said section of vessel to be harvested, a forward-motion tissue dissecting member coupled to the first end, and a backward-motion tissue dissecting member coupled to the second end. Preferably, the forward-motion tissue dissecting member includes an advancing edge that defines an angular configuration to facilitate advancing the instrument through the connective tissue and creation of a working space for the introduction of other harvesting tools or implements. The backward-motion tissue dissecting member includes means for engaging a side branch of the vessel section, such as a hooked element.

Yet another embodiment of the present invention provides a harvesting instrument having an elongated member with an end effector detachably secured to the distal end of the elongated member. The distal end includes a curved element having a distally-facing curved end for advancing distally along the vessel and being formed in a proximally facing portion which terminates in a proximally facing tip for engaging tissue when advanced proximally. The distal end also includes a proximally facing tissue cutting assembly supported within the proximal facing portion for dissecting the engaged tissue from the vessel when advanced proximally. Preferably, the tissue cutting assembly includes a pair of coacting blades pivotally supported by the proximally facing portion of the curved element. The coacting blades may be provided with monopolar or bipolar capability.

A method for minimally invasively harvesting a saphenous vein and the like associated with such an instrument is provided whereby the distal end of the instrument is introduced into an entry incision within the patient and advanced along the saphenous vein in a distal direction. The instrument is then retracted such that the distal end is advanced along the saphenous vein in a proximal direction while dissecting tissue from the vein. To this end, the distal end includes a backward-motion tissue dissecting means formed of a pair of confronting coacting blades oriented in the backward direction. The tissue is engaged with the coacting blades while retracting said distal end, and the coacting blades are actuated to dissect the tissue from the vein. Cauterization of the tissue may be performed by applying a voltage across the coacting blades when actuated to cause a current to flow selectively between the blades to promote hemostasis The various harvesting methods of the present invention provide for employment of the above embodiments, respectively, through one or more incisions made in the patient's body.

DETAILED DESCRIPTION OF THE INVENTION

The present invention is devices, various assemblies of components, and methods for the minimally invasive harvesting a section of a vessel from a patient's body. The section of vessel may be used, for example, as a coronary artery bypass graft. The following description of the present invention is primarily directed to the minimally invasive harvesting of the saphenous vein, however, it is contemplated and should be understood that other vessels and vascular conduits may be harvested using the devices and procedures of the present invention, Although the precise physiology may vary from patient to patient, the greater saphenous vein generally runs the length of the inner side of the leg and terminates at the groin, where it enter the femoral vein. Prior to harvesting the saphenous vein for a coronary artery bypass procedure, typically the right or left greater saphenous vein is chosen for removal following preoperative examination of the legs of the patient. The total length of vein section require artery bypasses to be performed coronary artery bypasses to be performed. A minimum length of 6 to 8 inches of saphenous vein is harvested for each bypass graft. When greater segments of a greater saphenous vein cannot be found, the lesser saphenous vein may then be used if it proves to be of adequate diameter. On rare occasions, suitable segments of vein cannot be found in either leg and another vessel or vessels are used. In addition to the left and right internal mammary arteries, these other vessels may include, for example, the gastroepiploic artery, the radial artery in the forearm, and the cephalic vein from the wrist to shoulder.

For harvesting of the saphenous vein, the initial incision may be made in the ankle or groin region or above or below the knee. The saphenous vein has a larger diameter in the groin region and is less fragile above the knee than below the knee. However, some physicians and nurses prefer to make the initial incision at the ankle because of the ease in locating the vein, better exposure, a less crowded workspace, and a decreased chance of wound infection because of the distal location from the groin.

The instrument and various components of the present invention are introduced through one or a small number of discrete incisions in any of these locations and are progressively advanced along the length of the vessel to be harvested. As the instrument is advanced, the main trunk of the saphenous vein is separated from the surrounding connective tissue and skin while each side branch or feeder vessel is carefully located and separated from the major vessel. Side branches occurring within the segment of the vessel to be harvested are separated at a point close to their entry into the main trunk, typically by the application of a suture, staples or surgical clip to secure the vessel and by severing the side vessel. The side branches may also be separated in a single step by cauterization. Before the vein is removed, placement of a marking suture may indicate its longitudinal position. The ends of the harvested vessel section are identified and secured prior to removal. The vessel section is then removed from its native location and placed in a basin of heparinized saline or other preservative solution until the coronary bypass anastomoses are performed.

Figure 1:
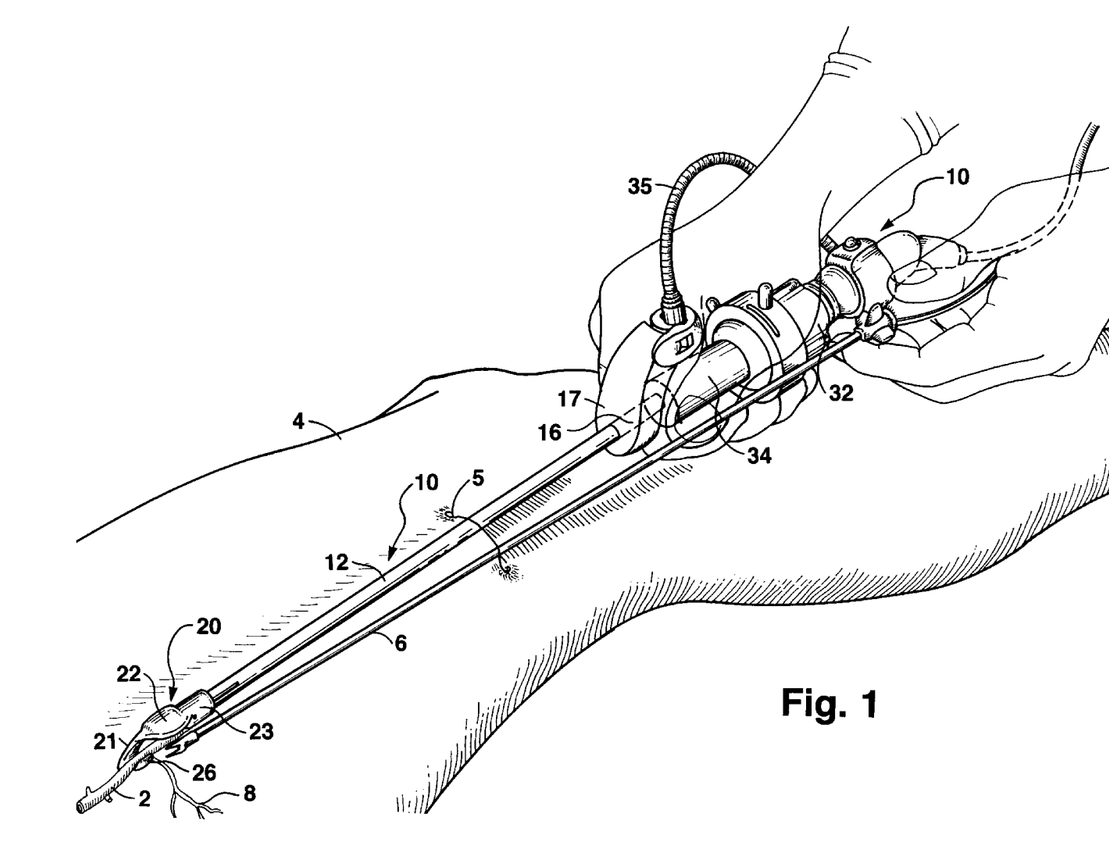
FIG. 1 illustrates one embodiment of the vessel harvesting device of the present invention operatively positioned within a patient's leg for harvesting a saphenous vein. This embodiment has an endoscope integrally coupled with the harvesting device and held together by a coupler mechanism.

Referring now to the drawings, wherein like elements have the same reference number throughout, the structures and methods of use of the vessel harvesting devices of the present invention are illustrated. FIG. 1 illustrates one embodiment of a vessel harvesting device 10 of the present invention being used to harvest a vessel, such as the saphenous vein 2, in the leg 4 of a patient. Here, harvesting device 10 has been introduced within leg 4 through a small surgical incision 5 over saphenous vein 2. Harvesting device 10 may be used in combination with other microsurgical instruments 6 and may incorporate an endoscope 30, as shown in FIG. 1, which may be of the type commonly used by surgeons for endoscopic surgery. The exterior of harvesting device 10 is smooth to reduce trauma to the surrounding tissue upon insertion and removal of the instrument from surgical incision 5.

Here, the proximal portion of endoscope 30 includes a lens portion 32 and illumination portion 35 operatively connected to an elongated body portion or scope tube 36 extending distally. Body portion 36 may be provided in varying lengths and cross-sections to accommodate patients of different sizes and to harvest vessel sections of different lengths. A fiber optic viewing means and lighting source (not shown) are provided at the distal end of elongated body portion 36 for viewing and illumination, respectively, of the area immediately adjacent the distal end.

Harvesting device 10 includes an elongated member 12 which, in various embodiments of the present invention, may have a cylindrical rod configuration or have a structure having a hollow lumen. As shown in FIG. 1, elongated member 12 is a tubular structure having a lumen extending between a first or distal end 14 and a second or proximal end 16 and having a length and cross-sectional dimensions sufficient to accommodate the body portion or scope tube 36 of endoscope 30, which is slideably engageable within the lumen of elongated member 12.

Figure 5:
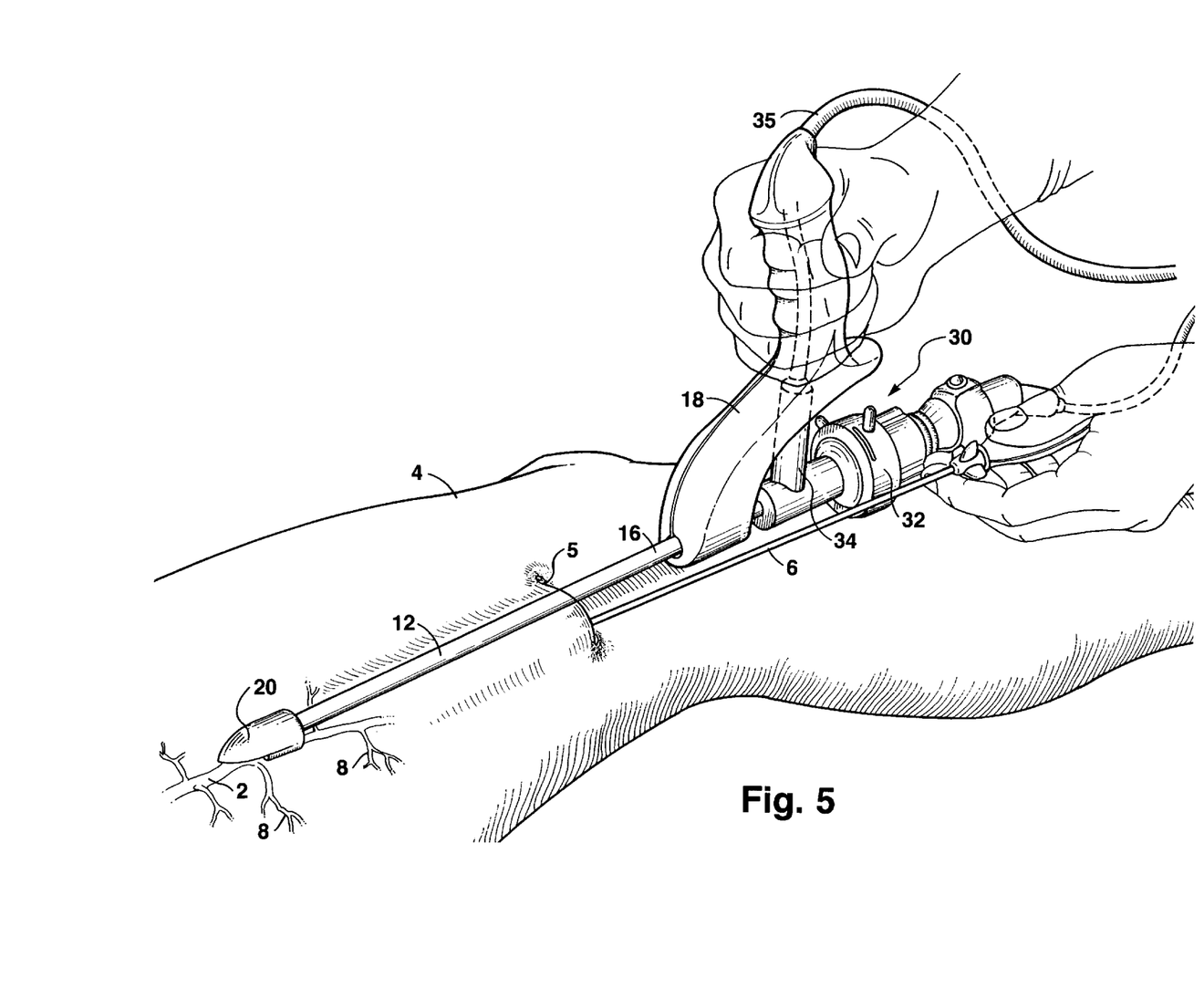
FIG. 5 illustrates another embodiment of the vessel harvesting device of the present invention operatively positioned within a patient's leg for harvesting a saphenous vein. This embodiment employs the end effector of FIG. 4A and is preferably manipulated in a forward motion in the direction away from the entry incision in order to separate or dissect the connective tissue and skin from the vein and create a working space for other tools. An endoscope is also shown integrally coupled with the harvesting device and held together by a handle mechanism.
Figure 6:
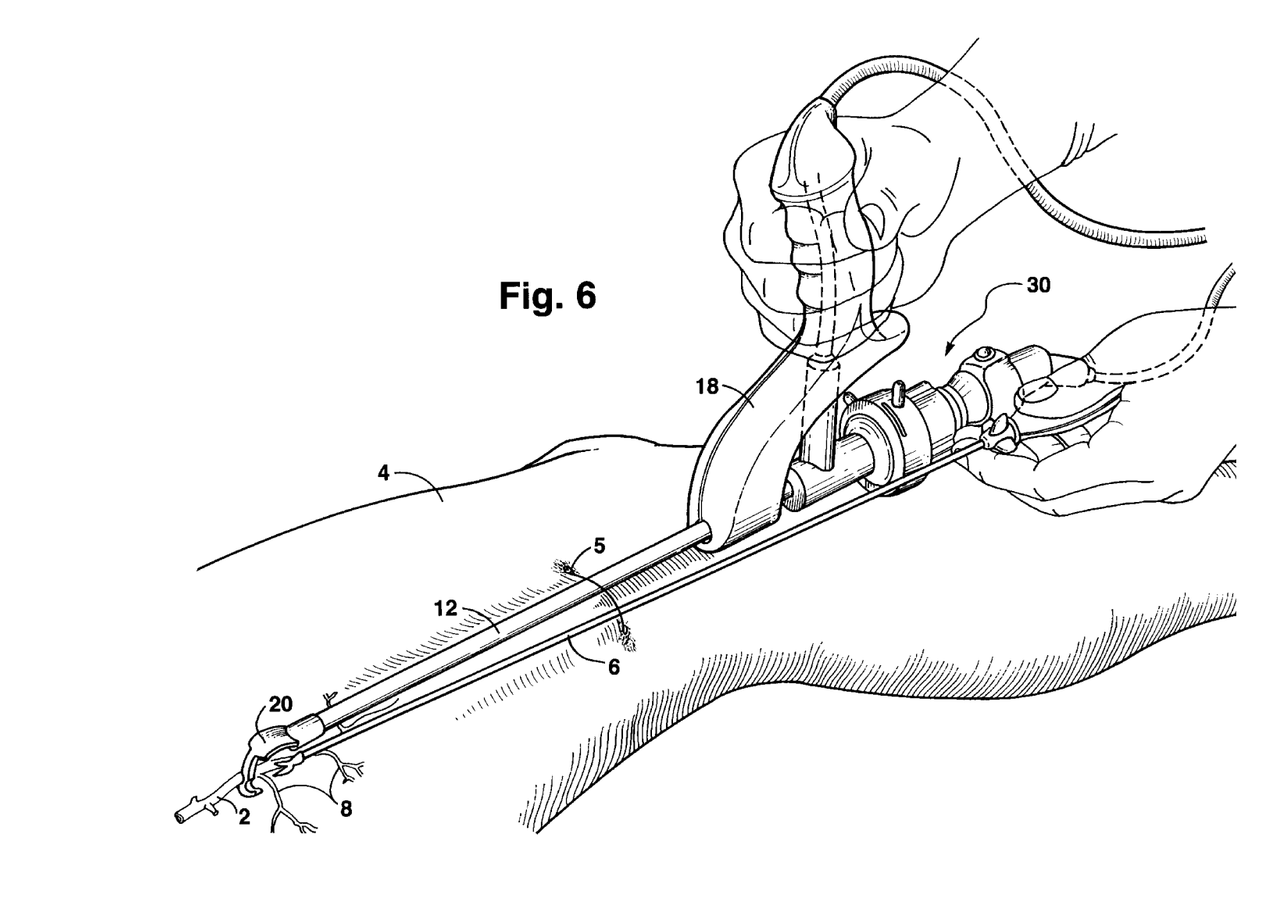
FIG. 6 illustrates another embodiment of the vessel harvesting device of the present invention operatively positioned within a patient's leg for harvesting a saphenous vein. This embodiment employs the end effector of FIG. 4B and is preferably manipulated in a backward motion in a direction toward the entry incision in order to engage side branch vessels and isolate them for removal by means of an optional auxiliary tool. An endoscope is also shown integrally coupled with the harvesting device and held together by a handle mechanism.

A coupler mechanism 17, discussed in more detail below with respect to FIGS. 9A–C and 10, is used to detachably couple elongated member 12 to endoscope 30. In other embodiments, such as in FIGS. 5–7, a handle mechanism 18 is attachable to the proximal end 16 of elongated member 12 and to endoscope 30, as shown having a lumen to accommodate a light transmission conduit 35, to fix the axial and rotational movement of elongated member 12 with respect to endoscope 30. Alternatively, one or both of elongated member 12 and endoscope 30 may have a dedicated handle mechanism to control and manipulate the axial and rotational movement of each independently of the other.

The overall length of elongated member 12 and the elongated body portion 36 of endoscope 30 may vary but should have at least the length required to access the most remote portion of the saphenous vein which is accessible through a minimally invasive incision. Elongated member 12 and body portion 30 are preferably at least as long as the section of vessel to be removed, for example, or have a length substantially the distance between the area below the groin to the area above the knee or between the area above the ankle to the area below the knee. Preferably, the length of elongated member 12 and elongated body portion 36 are from about 25 to about 35 cm (10 to 14 inches). Where a longer section of vessel is needed and where it is desirous to limit the number of incisions, longer instruments, including those that extend the entire length of the leg, may be employed.

Figures 2A, 2B, 3:
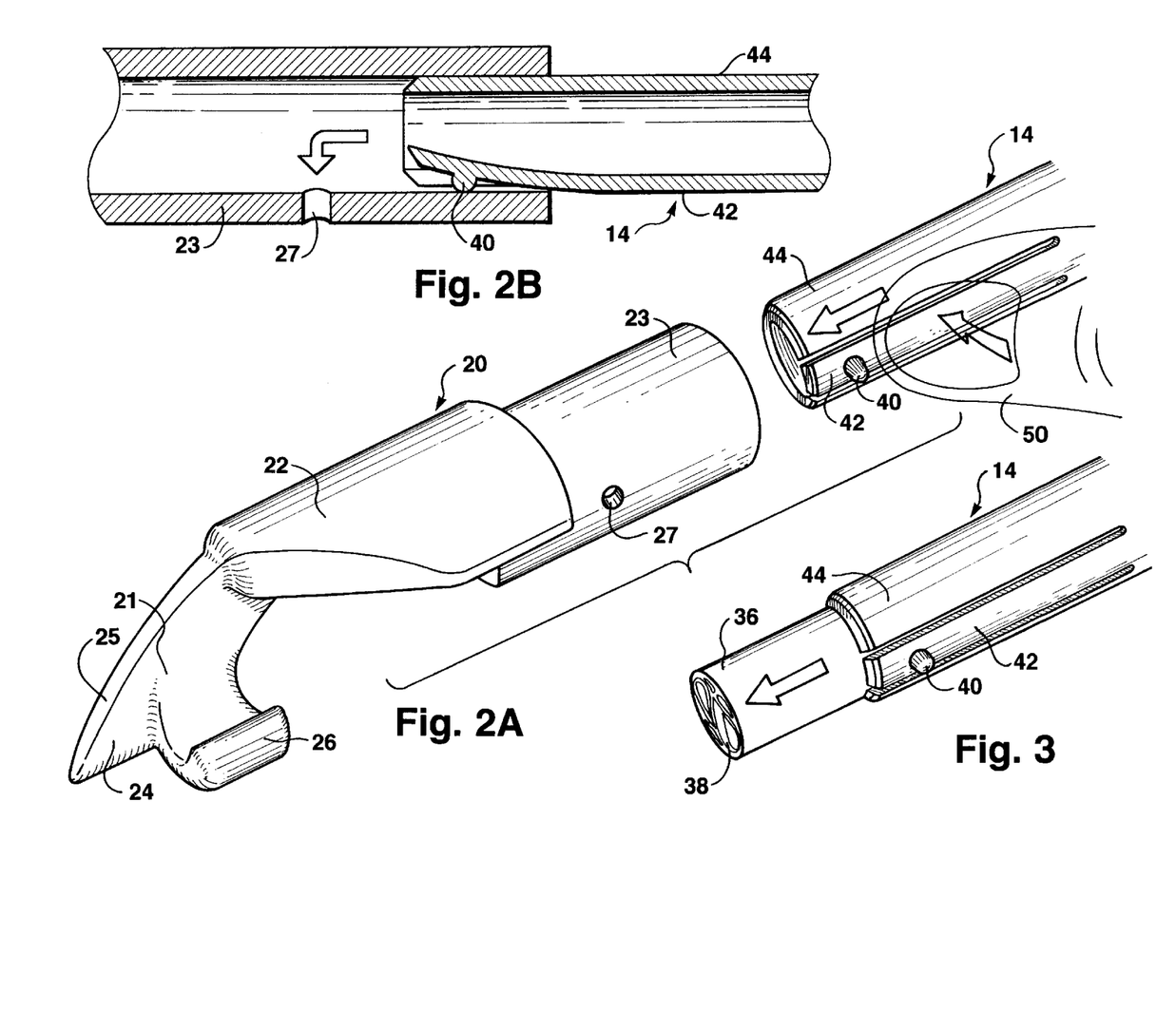
FIG. 2A is an enlarged view of the end effector of the embodiment shown in FIG. 1 and the distal end of the elongated tubular member to which the end effector is detachably mounted. This end effector is suitable for separating connective tissue and skin from a vessel to be harvested as well as for engaging side branch vessels to be severed.
FIG. 2B shows a cross-section of the engagement of an end effector to the distal end of the elongated tubular member of the harvesting device, and in particular, an exemplary means is shown by which the end effector is detachably mounted to the tubular member.
FIG. 3 is an enlarged view of the distal end of the elongated tubular member having an endoscope extending therethrough such that the viewing means of the endoscope extends distally of the distal end of the tubular member.

Mounted to the distal end 14 of elongated member 12 is one embodiment of an end effector or harvesting implement 20 of the present invention, which is more clearly shown in FIG. 2A. End effector 20 has several integral sections including a distal portion 21, a central portion 22, and a proximal portion 23. Distal portion 21 is provided with one or more structural elements for specific harvesting steps or techniques. For example, distal portion 23 has a distally extending angular configuration 24 with a leading or advancing or tissue dissecting edge 25 which facilitates the separation of connective tissue from saphenous vein 2 when harvesting device 10 is advanced distally or forward or in a direction away from the incision through which harvesting device 10 is introduced into the patient's leg 4. Located generally proximal to tissue dissecting edge 25 is a hooked element 26 for guiding end effector 20 along vein 2 and for engaging side branches 8 of vein 2. Hooked element 26 is particularly useful when moving harvesting device 10 proximally or backwards or in a direction toward the incision through which harvesting device 10 is introduced into the patient's leg 4. Hooked element 26 serves to further separate connective tissue from vein 2 as well as to isolate vein 2 from a side branch 8 while a ligating, cutting, or cauterizing tool 6 is used to separate vein 2 from side branch 8. Additionally, hooked element 26 is used to maintain engagement with the exterior of saphenous vein 2 such that the vein provides guidance for device 10 and endoscope 30 as it moves in either direction along the vein. The central portion 22 of end effector 20 has an enlarged nose portion or hub which acts as a shield for a viewing lens at the distal tip of endoscope 30 to prevent tissue from occluding the viewing lens as harvesting device 10 is advanced progressively along the length of the saphenous vein 2. Proximal portion 23 is configured for receiving an end 14 or 16 of elongated member 12. Proximal portion 23 is shown to have a lumen or aperture with a shape and size (cross-section) to accommodate distal end 14 and the viewing lens of elongated member 12.

End effector 20 of FIG. 2A is preferably detachably mounted to either end of elongated member 12. To effect this detachment capability, proximal portion 23 is provided with a bore or receptacle 27 through its housing for receiving a corresponding protrusion 40 on end 14 of elongated member 12. Protrusion 40 is positioned on a longitudinal portion or cutaway 42 of the housing 44 of elongated member 12. Housing 44 is preferably made of a relatively stiff material, such as stainless steel. Longitudinal cutaway 42 has a length such that it is flexible enough to be manually compressed (by the user's thumb 50, for example), as shown in the cross-sectional view of FIG. 2B, to provide clearance for protrusion 40 as distal end 14 is introduced within proximal portion 23 of end effector 20, but stiff enough to have a "spring bias" towards its original flush position. Thus, distal end 14 is advancable through proximal portion 23 of end effector 20 until protrusion 40 engages within receptacle 27 and becomes locked into place within proximal portion 23. Thereafter, insertion of the body portion 36 of an endoscope, as seen in FIG. 3, ensures that protrusion 40 remains engaged within receptacle 27, maintaining end effector 20 in fixed engagement to elongated tubular structure 12 during the harvesting procedure. Detachment of end effector 20 is accomplished, after sufficient retraction or withdrawal of endoscope 30, by pressing protrusion 40 or longitudinal cutaway section 42 with a finger or pusher tool (not shown) and pulling proximal portion 23 from elongated member 12. Other detachment and locking means, although not specifically described herein, may be used with the present invention.

Figure 4A:
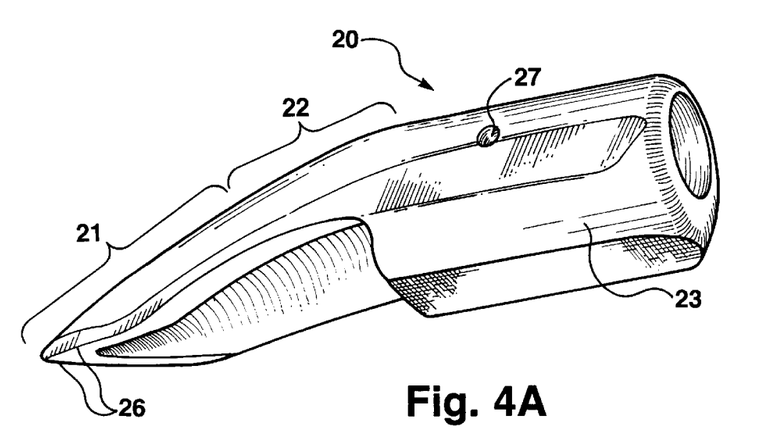
FIG. 4A is an enlarged view of another end effector which can be employed with the vessel harvesting device of the present invention; in particular, this end effector has a substantially angular configuration with a leading or advance edge suitable for dissecting or separating connective tissue and skin from the vessel being harvested. Such an end effector is most effective when manipulated in a forward motion or direction along the vein.
Figure 4B:
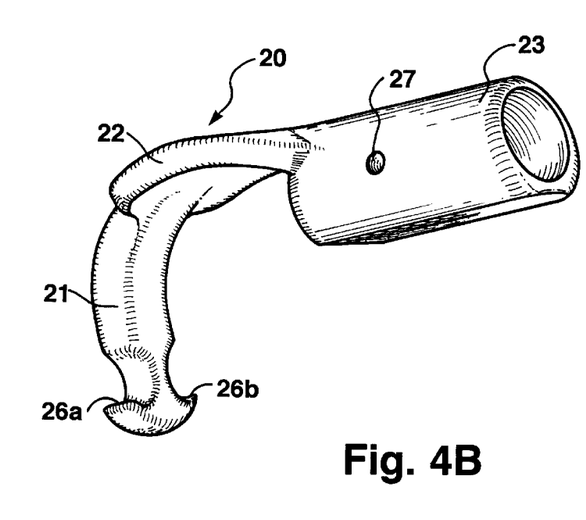
FIG. 4B is an enlarged view of yet another end effector which can be employed with the vessel harvesting device of the present invention; in particular, this end effector has two opposing hooked elements for engaging the vessel to be harvested as well as side branch vessels of the vessel. Such an end effector is most effective when manipulated in a backward motion or direction along the vessel.

Referring now to FIGS. 4A and 4B there are shown alternate embodiments of the end effector 20 of the present invention. In FIG. 4A, end effector 20 has a proximal portion 23 having a receptacle 27 similar to that of the end effector 20 of FIG. 2A. Central portion 22 acts to shield a viewing lens 38 when end effector 20 is operatively engaged with an endoscope. Distal portion 21 provides two tissue dissecting edges 25 which converge to define a substantially angular or pointed configuration to facilitate linearly advancing harvesting device 10 through intact tissue surrounding the vessel. Although only one and two dissecting edges 25 are illustrated in the drawings, it is contemplated that more than two, such as three, four, or more dissecting edges may be employed with the end effector 20 of the present invention. FIG. 4B shows an end effector 20 which has a distal extension 21 extending substantially perpendicular from central portion or shield 22 and has first and second vessel engaging means 26a, 26b which are comprised of curved surfaces that conform engagingly on either side to the exterior surface of the vessel. Depending on the positioning of the end effector 20 and the distal extension 21, the first 26a and second 26b vessel engaging means is drawn along the outside of the vessel until the opposite vessel engaging means encounters a side vessel or side branch (See FIG. 6). The first and second vessel engaging means 26a, 26b are preferably curved and may form hooks on either or both sides of the end effector 20. Alternately, distal extension 21 may provide only one vessel engaging means or more than two. Proximal portion 23 has a configuration similar to the previously discussed end effectors 20 to allow releasable detachment to a tubular structure 12.

Preferably, the end effectors 20 of the present invention are made of a plastic material such as acrylonitrile-butadiene styrene (ABS) or other similar material. The height, width, and length of the end effector may vary upon the vessel being harvested and the harvesting step to be performed. For example, for performing the step of separating connective tissue from harvesting of the saphenous vein, the embodiment of FIG. 4A may preferably have a height (at the point of greatest thickness) of approximately 1.2–1.4 cm, a width (at the point of greatest width) of approximately 2.2–2.4 cm, and a length of approximately 5.4–5.8 cm. For performing the step of engaging side branches or protecting or isolating the vein from tools being used to sever side branches from the vein, the embodiment of FIG. 4B may have a distal portion having a height of approximately 1.8–2.0 cm, a width (at the point of greatest width) of approximately 1.4–1.6 cm, and a length of approximately 3.6–4.0 cm. Likewise, the embodiment of FIG. 2A may be used for both of the mentioned steps and has similar dimensions as the embodiments of FIGS. 4A and 4B. Although only several particular end effectors 20 have been illustrated and described, it is contemplated that other similar end effectors and implements, having varying shapes, dimensions, number of dissecting edges and engaging elements, and functions are useable with the harvesting instrument of the present invention.

As the end effectors 20 are preferably removably attachable to elongated member 12, the various embodiments of end effectors 20 of the present invention may be interchangeable with each other and may be employed with a single elongated member 12. Alternatively, each end effector 20 may be permanently mounted to an elongated member 12 which is itself removably attachable to endoscope 30 and interchangeable with other end effector-elongated member pairs. For the latter configuration, coupler 17 or handle mechanism 18 may be used to effect quick and easy detachment and attachment of the harvesting implements to endoscope 3.

In other embodiments, an elongated structure 12 is provided having means at both ends for removably attaching and detachably mounting various end effectors 20. For example, the proximal end 16 of elongated structure 12 may have the same or similar configuration as distal end 14 of FIGS. 2A, 2B, and 3. With such a configuration, two end effectors 20, one at each end, may be detachably mounted to elongated structure 12. This configuration along with a coupling means, such as coupler 17, may also effect the quick and easy engagement and disengagement of an endoscope 30 within tubular structure 12.

Figure 9A:
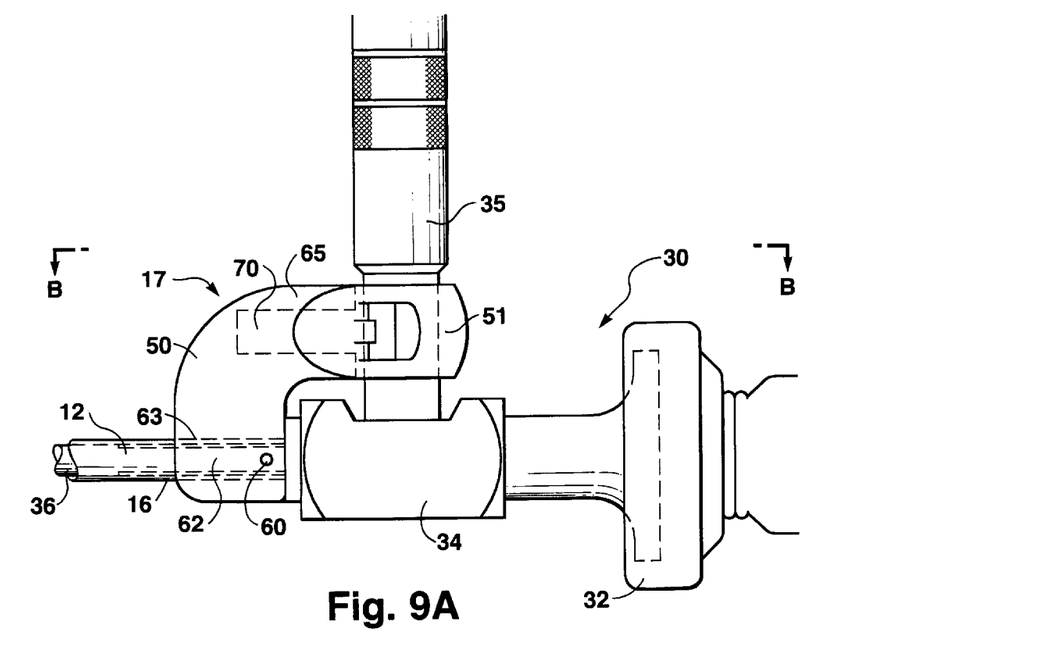
FIG. 9A is a side view of the integral engagement of the elongated tubular structure and an endoscope by means of a coupler mechanism of the present invention.
Figure 9B:
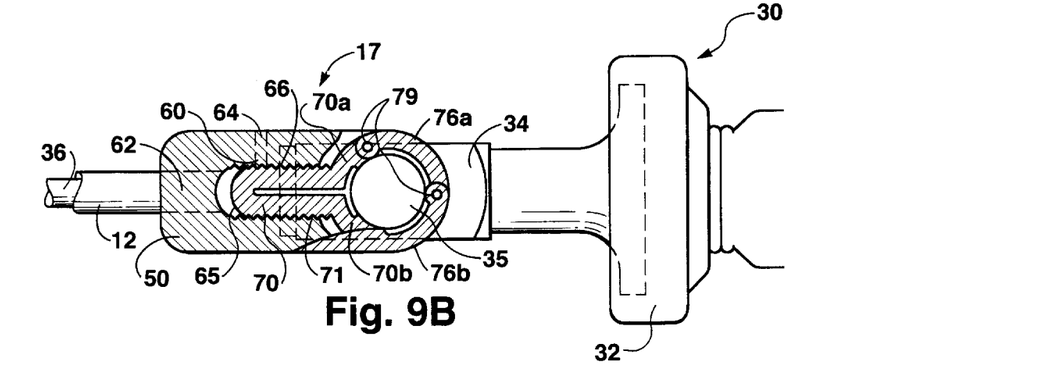
FIG. 9B is a top view of a cross-section of FIG. 9A taken along the line B—B which illustrates the coupler mechanism in a closed and locked position.

Turning to FIGS. 9–10, and FIGS. 9A–C in particular, there is shown a coupler mechanism 17 detachably coupling an endoscope 30 with the proximal end 16 of tubular structure 12. To accommodate such coupling, proximal end 16 has an longitudinal cutaway portion 62 (shown in phantom in FIG. 9A) having a protrusion 60 extending therefrom, similar to longitudinal cutaway portion 42 and protrusion 40 of distal end 14 (FIG. 2A) but on the opposite side of the elongated structure 12. Coupler 17 includes a sleeve member 50 and a clip 51 which may be made of the same or similar material as that of end effectors 20. Sleeve member 50 has a first bore 63 therethrough for axially receiving tubular structure 12 and scope tube 36 of endoscope 30. In FIG. 9B, which is a top view of FIG. 9A taken along the lines BB, a smaller, second bore 64 extends radially from bore 63 to receive protrusion 60 of proximal end 16 of tubular structure 12. As with distal end 14, longitudinal cutaway portion 62 can be compressed to allow insertion of proximal end 16 into first bore 63 until protrusion 60 becomes engaged within second bore 64. Likewise, longitudinal cutaway portion 62 can be depressed to remove tubular structure 12 from coupler 17.

Additionally, sleeve member 50 has a female end portion 65 having internally extending teeth 66 for receiving a male end portion 70 of clip 51 having corresponding teeth 71. Male end portion 70 has a "U-shaped" configuration such that compressing or squeezing end portion 70 allows a selected length of end portion 70 to be inserted into female end portion 65. When released, male end portion 70 expands to its normal width, and teeth 71 engage with teeth 66 of female end portion 65 to secure the two together and prevent any rotational or axial movement between them. As both female end portion 65 and male end portion 70 have teeth over their entire lengths, respectively, the length of male end portion 70 inserted can be selected to accommodate endoscopes of varying configurations, and particularly differences in the distal length of the connector portion 34.

Figure 9C:
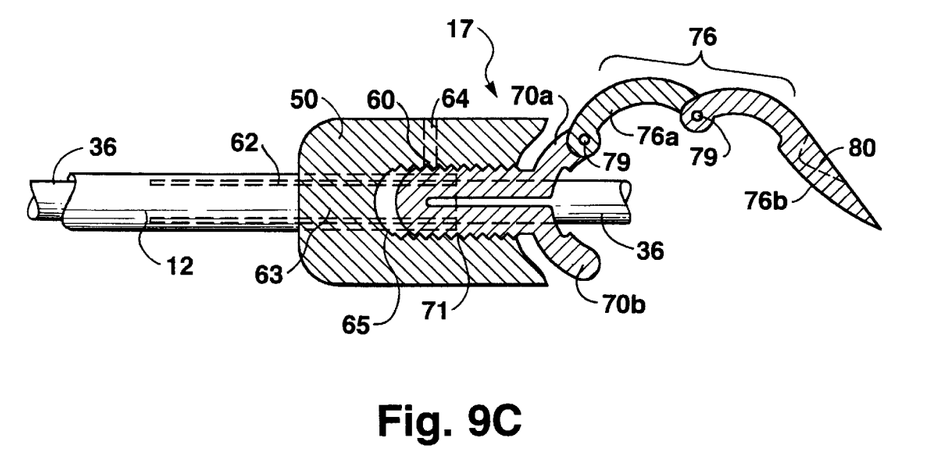
FIG. 9C is the a top cross-sectional view of the coupler mechanism in an open position.
Figure 10:
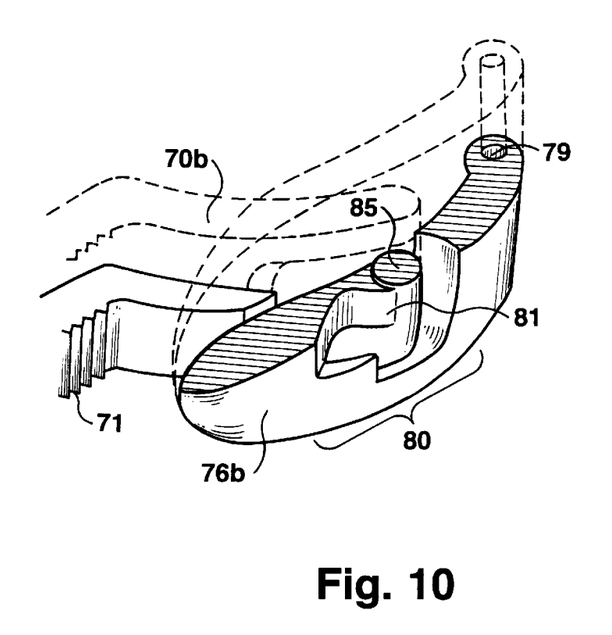
FIG. 10 is a schematic perspective view of an exemplary locking mechanism of the coupler mechanism.

Male end portion 70 of clip 51 terminates at first and second tips 70a and 70b, respectively. As shown in FIG. 9C, a segmented arm 76 extends from tip 70a of end portion 70. Segmented arm 76 includes two annular segments, a proximal segment 76a and a distal segment 76b. Annular segment 76a is coupled to first tip 70a of end portion 70 and to distal segment 76 by means of pins 79. In a closed position, as shown in FIG. 9B, arm 76 encircles light transmission conduit 35 of endoscope 30 to fix the axial and rotational movement of endoscope 30 with respect to tubular structure 12. As shown in the cross-sectional view of FIG. 9C, proximal annular segment 76b is provided with a locking means, and particularly in this example, an over-center mechanism 80 for snap-fitting with second tip 70b of male end portion 70. Over-center mechanism 80 includes a flexure element 81 which frictionally engages an annular surface 85 of second tip 70b when in a locked position. Segmented arm 76 is unlocked by pulling outward on annular segment 76b, with a finger tip, for example.

Thus, the configuration of ends 14 and 16 of tubular structure 12 and the respective configurations of the end effectors 20 and coupler 17, allow interchangeablility between end effectors at each end. Further, such a configuration, along with coupling mechanism 17 (although not required), provides a user with the versatility to introduce, and lock into position, an endoscope 30 through either end of elongated structure 30. Thus, an aspect of the present invention is a harvesting system or an assembly of harvesting components which includes a harvesting device 10 with a plurality of interchangeable harvesting implements 20 to provide flexibility and optimization of the vessel harvesting procedure.

The particular procedural steps for using a harvesting instrument 10 employing one or more end effectors 20, and with or without an endscope 30, may be slightly different depending upon the number and type of end effectors used as well as the number of entry incisions employed. For example, the device 10 of FIG. 1, which employs the multi-purpose end effector 20 of FIG. 2A having both forward and backward dissecting elements, reduces the number of instruments necessary to harvest the vessel and the number of times that a harvesting device 10 is removed and reinserted for replacement of an end effector.

In use, device 10 of FIG. 1 is inserted through a single entry incision 5, which is shown to be just above the knee but may be proximate the groin, below the knee, or proximate the ankle. Upon exposure of the vein 2 and an initial transection of the tissues in the immediate region, the distal end of end effector 20 and the distal end of endoscope 30 are contemporaneously introduced into entry incision 5. Harvesting device 10 is pushed or guided along the saphenous vein 2 in a direction away from entry incision 5 so as to manipulate end effector 20, and particularly tissue dissecting edge 25, to separate connective tissue from saphenous vein 2 and to create a working space for the manipulation of other tools 6. After traversing the section of vein 2 to be removed with this forward-motion dissection, device 10 may be pulled or guided along vein 2 in a backward or proximal direction toward entry incision 5. End effector 20, and particularly hooked element 26, is manipulated to further dissect vein 2 from connective tissue and to engage side branches 8 and isolate or protect vein 2 from other harvesting tools 6 used to separate side branches 8 from vein 2. As shown in FIG. 1, a tool 6 is introduced through the same entry incision 5 through which device 10 is introduced. However, an additional incision may also be employed closer to the groin area, through which a tool 6 may be introduced. Alternately, device 10 may be introduced through this second incision, and tool 6 may be introduced through incision 5. One or more of these steps may be performed while continually viewing the saphenous vein 2 and the area immediately adjacent the viewing lens 38 of endoscope 30.

Particularly for the embodiments of FIGS. 4A and 4B, the interchangability of the respective end effectors 20 optimizes the harvesting procedure. For example, the end effector 20 of FIG. 4A is preferably employed for the initial separation of connective tissue from the saphenous vein 2 and manipulated along the vein 2 in a forward direction, away from the incision through which end effector 20 was introduced. Conversely, the embodiment of FIG. 4B is preferably employed after the initial separation of connective tissue from saphenous vein 2. Hooked elements 26 may be alternately engaged with vein 2 so as to locate side branches 8 extending from vein 2 in all directions. Additionally, hooked elements are used to isolate vein 2 while ligating, cutting, clipping, or cauterizing the side branches 8 with accessory tools 6. In application, this end effector 20 is preferably manipulated along the saphenous vein 2 in a backward direction towards the entry incision.

The particular procedural steps for using a harvesting instrument 10 employing the interchangeable end effectors 20 of FIGS. 4A and 4B may be slightly different depending upon the number of entry incisions used. For example, should only one entry incision be employed, such as entry incision 5 in FIGS. 5 and 6, the entire length of the tubular member 12 and the body portion 36 of endoscope 30 must be removed prior to detachment of a first end effector 20 from and attachment of a second end effector 20 to the distal end 14 of harvesting instrument 10. More specifically, the harvesting instrument 10, having a first end effector 20, such as the embodiment of FIG. 4A, mounted to distal end 14, is introduced into incision 5. After manipulating the first end effector 20 as it is intended to be used, instrument 10 is removed from incision 5 and the first end effector 20 is detached from instrument 10 in the manner discussed with respect to FIG. 2B. Next, a second end effector, such as the embodiment of FIG. 4B, is mounted onto distal end 14 of instrument 10 in the manner discussed with respect to FIG. 2B. The second end effector 20 is introduced into the same incision 5, and manipulated as described above.

Figure 7:
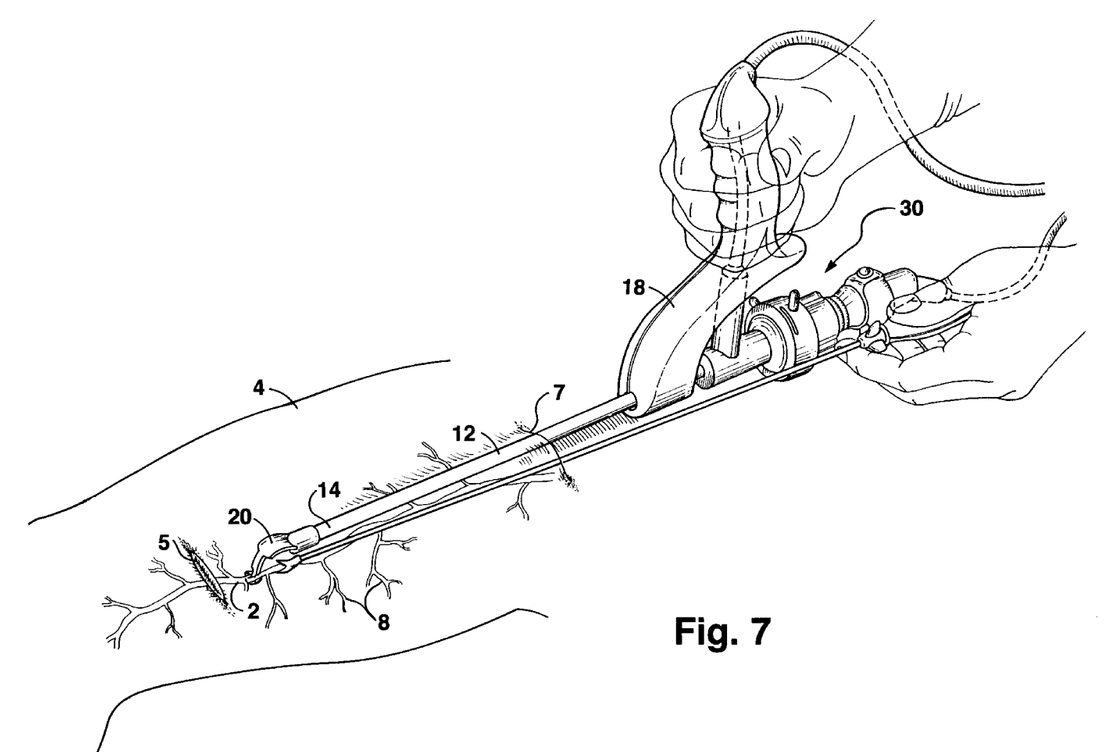
FIG. 7 is another illustration of the embodiment of FIG. 6 operatively positioned within a patient's leg for a harvesting procedure in which two surgical incisions are employed for insertion of the present invention and other harvesting implements.

In the situation where two (or possibly more) incisions are employed, typically one at each end of the section of vessel to be harvested as seen in FIG. 7, there is no need to completely remove the entire length of elongated portion 12 and endoscope 30 from leg 4. Instead, after having been introduced through the first incision 7 and traversed along the saphenous vein 2, distal end 14 may simply be exposed or protruded through the second incision 5 and the first end effector 20 detached from instrument 10. While still protruding form the second incision 5, the second end effector 20 is mounted to distal end 14 and then guided along vein 2 towards the first incision 7. This procedure is likely to minimize trauma to the harvested vessel as well as to the surrounding tissue as it reduces the number of times that the harvesting instrument is inserted and removed from the leg. Alternatively, with two incisions as described above, harvesting instrument 10 and the attached end effectors 20, as well as endoscope 30 and other tools 6, may be inserted through either entry incision as needed to optimize access of the vein 2 and side branches 8.

Figure 8:
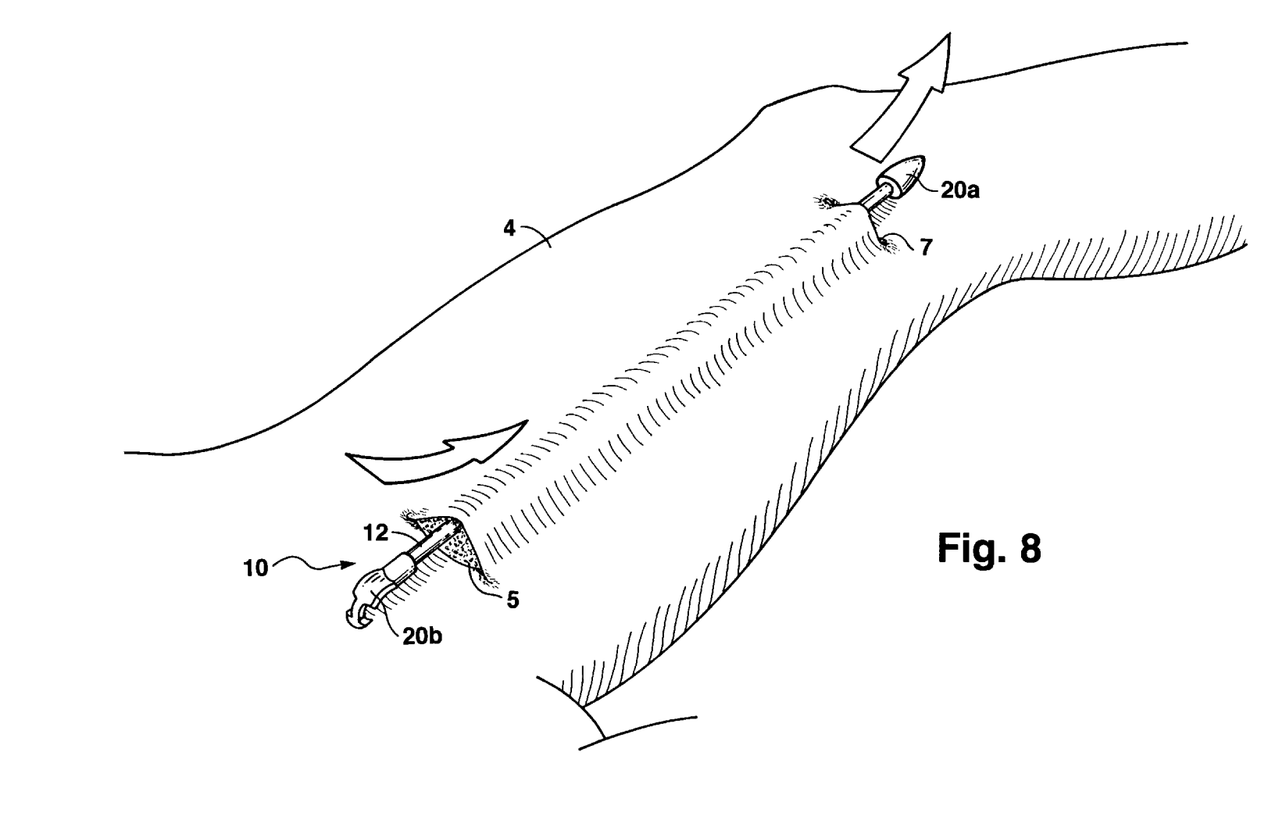
FIG. 8 shows yet another embodiment of the vessel harvesting device of the present invention operatively positioned within a patient's leg for harvesting a saphenous vein. This embodiment has two end effectors, one mounted to each end of the elongated tubular member. The end effectors are of the type shown in FIGS. 4A and 4B, respectively.

Turning now to FIG. 8, there is shown another embodiment of the harvesting instrument 10 of the present invention operatively positioned within the leg 4 of a patient. As illustrate elongated embodiment includes a harvesting device 10 having an elongated rod or tube 12 extending between two ends and having a length substantially equal to or greater than that of the section of vessel to be harvested. At one end, an end effector 20a of the type illustrated in FIG. 4A is attached, and at the opposite end, an end effector 20b of the type illustrated in FIG. 4B is attached. The end effectors 20a and 20b may be detachable so as to facilitate the use of an endoscope with harvesting device 10. However, it is contemplated that an endoscope may be used with both end effectors attached and without necessitating removal of one of them for integral coupling of an endoscope.

The embodiment of FIG. 8 is employed in a minimally invasive harvesting procedure using one or more incisions over the section of vessel to be extricated. With only one incision, the manner of use is similar to that described with respect to FIGS. 5 and 6. In a procedure using two incisions, end effector 20a is inserted into a first incision 5. By handling the opposite end of elongated structure 12 and pushing it in a direction from the first incision 5 to a second incision 7, end effector 20a is manipulated along the saphenous vein toward the second incision 7 to separate the vein 2 from its connective tissue. Upon being advanced the distance between the first and second incisions, end effector 20a is grasped and pulled in a direction from the first incision 5 to the second incision 7 such that end effector 20b is manipulated along the vein 2 to further separate it from connective tissue and facilitate the separation of side branches. Finally, harvesting instrument 10 may be removed from the second incision, and the process repeated through either incision as necessary. Additionally, the harvesting device may be introduced into the second incision 7 to harvest another section of vein 2, such as in the patient's lower leg. Alternatively, one or more incisions may be made in the lower leg to facilitate the harvesting procedure.

Figure 11:
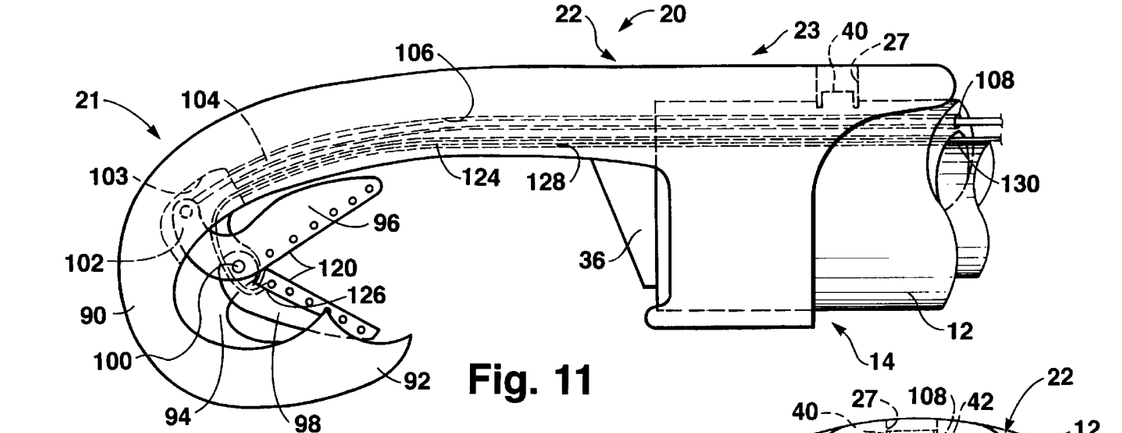
FIG. 11 is an enlarged side view illustrating an alternative embodiment of the end effector which can be employed with the vessel harvesting device in accordance with the present invention; in particular the end effector has a backward-facing scissors mechanism which is effective when manipulated in a backward direction along a vessel.
Figure 12:
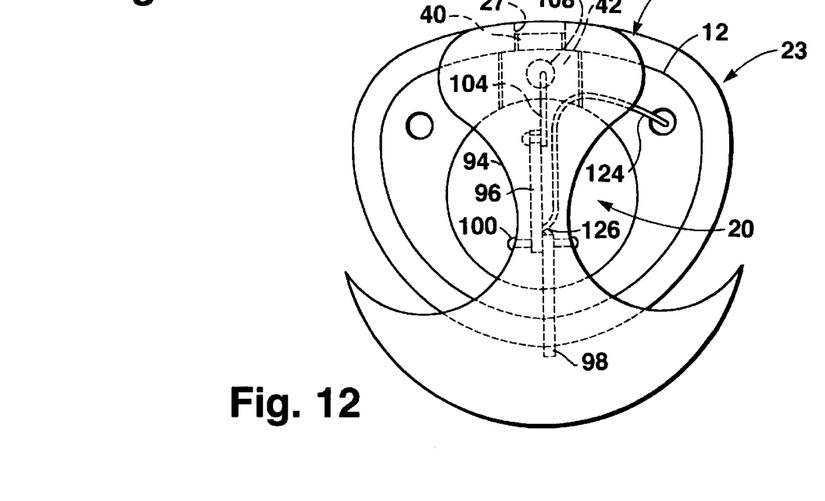
FIG. 12 is an enlarged end view of the end effector of FIG. 11.
Figure 13:
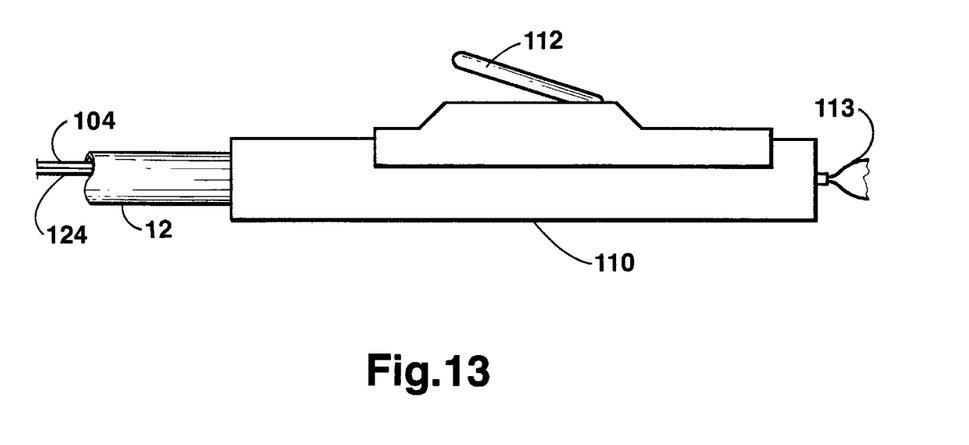
FIG. 13 is a side view illustrating a handle configuration which may be employed to actuate the scissors mechanism of FIGS. 11 and 12.

Referring to FIGS. 11–13 there is illustrated still another embodiment of an end effector or harvesting implement 20 of the present invention which is particularly useful for separating side branches and connective tissue from the saphenous vein. This embodiment is particularly adapted for use when moving the harvesting device 10 proximally, that is, in a direction toward the incision through which the instrument is introduced into the patient's leg 4. As may be seen, the embodiment provides an instrument which performs the function of dissecting side branches from a saphenous vein and the like as it is moved backward or proximally. Thus the embodiment of FIGS. 11–13 replaces the ligating, cutting or cauterizing tool 6, such as described in FIGS. 1, 5, 6 and 7, and thereby eliminating the need for additional tools and, thus, the use of an additional hand and possibly an additional surgeon or nurse which in turn minimizes the generally crowded conditions at the surgical site.

Referring to FIG. 11, the end effector 20 includes a distal portion 21, a central shielding portion 22 and a proximal portion 23. The end effector is detachably mounted to either end of the elongated member 12, as previously described in the embodiments of FIGS. 2–8, via the bore 27 in the proximal portion 23 and the corresponding protrusion 40 in the cutaway 42 of the distal end 14 of the member 12. As previously depicted in FIG. 3, the body portion 36 of an endoscope is inserted through the lumen in the elongated member 12 to provide illumination and visualization of the working distal portion 21 of the end effector 20, described below. The body portion 36 also ensures that the protrusion 40 remains engaged within the bore 27 to maintain the end effector 20 securely in place during the harvesting procedure.

The end effector 20 of FIGS. 11–13 is mounted to the distal end 14 of the elongated member 12 via a lumen with a shape and size (cross-section) which accommodates the distal end 14 of the member 12 as previously described in FIGS. 2A, 2B and 3. As in the previous embodiments, the end effector 20 of FIGS. 11–13 is provided with its specific alternative structural elements particularly configured to facilitate the dissection of side branches from, for example, a saphenous vein, thus replacing the microsurgical ligating or cutting instrument 6 of the previous figures.

To this end, the central portion 22 of the end effector 20 preferably is widened in the region immediately above the distal viewing end of the endoscope's body portion 36 to act as a shield which prevents tissue from occluding the viewing end. The distal portion 21 extends distally from the central portion 22 to define a semi-spherically curved or U-shaped configuration. The end 90 of the distal portion 21 curves back proximally towards the distal end 14 of the elongated member 12 to define a proximally facing tip 92 for engaging or gathering a vessel's side branches and other connective tissue. A radially inwardly extending web 94 is formed in the inner curvature of the distal portion 21 to provide support for a pair of cooperating cutting blades 96, 98 defining a microsurgical scissors instrument. As may be seen, the cutting blades 96, 98 are mounted on the support web 94 within the curved distal portion 21 facing the viewing end of the endoscope body 36, that is, facing proximally. Blades 96, 98 may be curved or straight along their confronting cutting edges as desired. As depicted in FIGS. 11–13, the lower blade 98 is held stationary while the upper blade 96 is pivotable downwardly about a pin 100 to effect the cutting process. It is understood that the functions of the blades can be reversed, with the lower blade pivoting upward against a stationary upper blade. The blade 96 includes an integral member 102 extending generally perpendicularly from the pivot area portion of the blade 96. The member 102 is disposed for movement within a suitable cut-out portion 103 formed in the inner curvature of the distal end 21. A cord, wire or cable 104 is attached to the end of the member 102 via a suitable knob or pin, whereby translation of the cable 104 in a proximal direction imparts pivoting of the upper blade 96 towards the lower blade 98 to effect the cutting process. As depicted in phantom line in FIGS. 11–13, the cable 104 extends from the member 102 through a suitable lumen 106 in the end effector 20 and through a longitudinally extending lumen 108 in the wall of the elongated member 12. The proximal end of the cable 104 extends to a handle mechanism 110 and particularly is connected to a pivotable lever or member forming part of a handle actuator 112 operable by a surgeon (FIG. 13). In a bipolar scissor configuration of the invention, the cable 104 is made of an electrically conductive material to allow it to also be used as an electrical conductor, as further described below.

In operation, the microsurgical instrument including the end effector 20 of the invention depicted in FIGS. 11–13, is advanced through an entry incision 5 or 7 (FIGS. 1, 5–8), and along the section of the saphenous vein 2 to be harvested. In the process of dissecting the side branches 8 from the vein 2, the instrument, and particularly the end effector 20 attached thereto, is retracted proximally towards the entry incision to allow the open blades 96, 98 of the end effector 20 to engage the side branches. Actuation of the actuator 112 closes the blades 96, 98 to dissect the engaged side branch 8 from the vein 2.

The description above illustrates an end effector 20 in which the blades 96, 98, and thus the cutting or dissecting process, has been described in a manner that generally implies it is primarily a mechanical device and process. However, the microsurgical scissor apparatus thereof preferably employs bipolar or monopolar energy which is applied to the blades 96, 98 to cauterize while simultaneously cutting the tissue, side branches, etc., during the dissection process. The application of bipolar or monopolar capabilities to the surgical instrument of the present invention is commonly known in the art.

FIG. 11 illustrates a possible configuration for the application of bipolar energy. A first cable 104, discussed above, may act as a conductor for energy of one polarity to be applied to one or both blades 96, 98. A second conductor wire 124, which is connected to one or both blades 96, 98 via weld points 126 (FIGS. 11 and 12), may act as a conductor for energy of the polarity opposite to that of cable 104. The conductor wire 124 extends through respective lumens 128, 130 in the end effector 20 and the elongated member 12, with the proximal end of the wire 124 extending to the handle mechanism 110 depicted in FIG. 13. The handle mechanism 110 may be similar to the handle 2 of previous description in FIGS. 1A, 1B, 5A and 6 of this application. The proximal ends of the conductor wire 124 and of the cable 104 are selectively coupled within the handle mechanism 110 to a voltage source, such as to the bipolar terminals (of opposite polarity) of a commercially available RF energy source (not shown), which is coupled to input conductors 113 at the proximal end of the handle. It is contemplated that the instrument of the present invention be configured such that the entirety of blades 96, 98 are oppositely polarized from each other or such that each blade 96, 98 is provided with at least two electrodes whereby one electrode on each blade is oppositely polarized with respect to the other electrode on the same blade and similarly polarized as one electrode on the other blade.

In operation, when blades 96, 98 come into contact with tissue or side branches to be cut, the RF energy is selectively supplied to blades 96, 98 by the surgeon via the actuator 112. The extent of current flow through the connecting tissue in this situation may vary depending on the tissue type, position, thickness and the extent to which the tissue is under tension. The current flow between the blades 96, 98 causes hemostasis in tissue contacting the surfaces of the blades 96, 98; that is, causes the arrest of bleeding including coagulation and cauterization.

Although the devices and methods of the present invention have been described in some detail by way of illustration and example, it will be readily apparent to those skilled in the art that certain modifications and other embodiments may be practiced without departing from the spirit and scope of the invention and which are within the scope of the appended claims.

What is claimed is:

1. A vessel harvesting apparatus comprising an elongated member having distal and proximal ends, handle means selectively coupled to said proximal end of said elongated member, and an end effector detachably secured to said distal end of said elongated member, comprising:

a curved element having a distally-facing curved end for advancing distally along the vessel;

said curved element being formed in a proximally facing portion which terminates in a proximally facing tip for engaging tissue when advanced proximally; and a proximally facing tissue cutting assembly supported within said proximal facing portion for dissecting the engaged tissue from the vessel when advanced proximally.

2. The apparatus of claim 1 wherein said tissue cutting assembly includes a pair of coacting blades pivotally supported by said proximally facing portion of said curved element and operable to dissect the engaged tissue when advanced proximally.

3. The apparatus of claim 2 wherein one of said coacting blades is stationary and the other is pivotable when actuated to engage said stationary blade.

4. The apparatus of claim 3 wherein said elongated member includes a lumen within a sidewall thereof, including:

an integral member integrally formed with said pivotable blade; and actuating means extending through said lumen and having a distal and a proximal end, and coupled at a distal end with said integral member, and responsive to an actuating force applied via said handle means to said proximal end for actuating said pivotable blade.

5. The apparatus of claim 4 wherein said actuating means includes a flexible wire or cable.

6. The apparatus of claim 2 including:

a voltage source; and wherein said coacting blades include at least one electrode adapted for connection to said voltage source to cause a flow of current between said blades to promote hemostasis in said dissected tissue.

7. The apparatus of claim 6 wherein said voltage source is monopolar.

8. The apparatus of claim 6 wherein said voltage source is bipolar.

9. The apparatus of claim 6 wherein:

said elongated member includes a lumen within a sidewall thereof; and linkage extending through said lumen and operably coupled to said blades and handle means for actuating said blades, said linkage being of electrically conductive material for electrically coupling said electrode to said voltage source.

10. The apparatus of claim 2 wherein said elongated member includes a tubular configuration having a lumen sized to accommodate an endoscope, said endoscope having an elongated body portion extending through said lumen and having a viewing means at a distal end for viewing said curved element and said coacting blades.

11. The apparatus of claim 1 wherein said proximal facing portion is U-shaped.

12. A method for minimally invasively harvesting a saphenous vein and the like comprising the steps of:

introducing a distal end of a vessel harvesting instrument into an entry incision, said distal end including a backward-motion tissue dissecting means formed of a pair of confronting coacting blades oriented in the backward direction;

advancing said distal end along the saphenous vein in a distal direction; and retracting said distal end along the saphenous vein in a proximal direction while dissecting tissue from the vein with said pair of confronting coacting blades oriented in the backward direction.

13. The method of claim 12 including the steps of:

engaging the tissue with said coacting blades while retracting said distal end; and actuating said coacting blades to dissect the tissue from the vein.

14. The method of claim 13 including the steps of:

applying a voltage across said coacting blades when actuated to cause a current to flow selectively between said blades to promote hemostasis in the engaged tissue.

* * * * *